US00PP19640P3

(12) United States Plant Patent
Johnson

(10) Patent No.: US PP19,640 P3
(45) Date of Patent: Jan. 20, 2009

(54) ***GRISELINIA* PLANT NAMED 'GREEN HEDGEMASTER'**

(50) Latin Name: *Griselinia littoralis*
Varietal Denomination: Green Hedgemaster

(76) Inventor: Tom Johnson, 26 Totara Road, Whenuapai, Auckland (NZ)

( * ) Notice: Subject to any disclaimer, the term of this patent is extended or adjusted under 35 U.S.C. 154(b) by 0 days.

(21) Appl. No.: 11/880,054

(22) Filed: Jul. 19, 2007

(65) Prior Publication Data

US 2008/0184413 P1 Jul. 31, 2008

(30) Foreign Application Priority Data

Jul. 31, 2006 (NZ) ..... TMR 086

(51) Int. Cl.
*A01H 5/00* (2006.01)

(52) U.S. Cl. ..... Plt./226

(58) Field of Classification Search ..... Plt./226
See application file for complete search history.

(56) References Cited

PUBLICATIONS

Griselinia littoralis, National Museums Northern Ireland, 2001,[online], [retrieved on Apr. 29, 2008]. Retrieved from the Internet <http://www.habitas.org.uk/gardenflora/griselinia.htm> one page.*

* cited by examiner

*Primary Examiner*—Annette H Para
*Assistant Examiner*—June Hwu

(57) ABSTRACT

A new cultivar of *Griselinia* plant named 'Green Hedgemaster' that is characterized by flat rounded leaves, a semi-upright habit and medium green leaves.

1 Drawing Sheet

Botanical classification: *Griselinia littoralis*.
Variety Denomination: 'Green Hedgemaster'.

BACKGROUND OF THE INVENTION

The present invention relates to a new and distinct cultivar of *Griselinia* plant botanically known as *Griselinia littoralis* and hereinafter referred to by the cultivar name 'Green Hedgemaster'.

The new cultivar is a naturally occurring branch mutation of *Griselinia littoralis* 'Variegate' (not patented). 'Green Hedgemaster' was discovered by the inventor in an outdoor field in a cultivated area of Auckland, New Zealand in 2002.

Asexual reproduction by tip cuttings of the new cultivar Green Hedgemaster was first performed in 2004 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Griselinia* cultivar 'Green Hedgemaster'.

1. *Griselinia* 'Green Hedgemaster' exhibits flat rounded leaves.
2. *Griselinia* 'Green Hedgemaster' exhibits a semi-upright habit.
3. *Griselinia* 'Green Hedgemaster' exhibits medium green leaves.

The new cultivar 'Green Hedgemaster' is distinguishable from the parent plant by the following characteristics:

1. 'Green Hedgemaster' has solid green leaves. The leaves of 'Variegata' are variegated.

2. 'Green Hedgemaster' has longer orbicular shaped leaves. The leaves of 'Vareigata' are shorter and are elliptic shaped.
4. 'Green Hedgemaster' is more vigorous.
5. 'Green Hedgemaster' has a shorter crop time.

The closest comparison cultivars are *Griselinia* 'Broadway Mint' (not patented) and *Griselinia* 'Whenauapai' (not patented).

The new cultivar 'Green Hedgemaster' is distinguishable from 'Broadway Mint' by the following characteristics:

1. 'Green Hedgemaster' has shorter leaves.
2. 'Green Hedgemaster' has an orbicular leaf shape. The leaves of 'Broadway Mint' are longer and are oval shaped.
3. 'Green Hedgemaster' is more vigorous.

The new cultivar 'Green Hedgemaster' is distinguishable from 'Whenauapai' by the following characteristics:

1. 'Green Hedgemaster' has longer orbicular shaped leaves. The leaves of 'Whenauapai' are shorter and are elliptic shaped.
2. 'Green Hedgemaster' is more vigorous.
3. 'Green Hedgemaster' has darker green leaves.

BRIEF DESCRIPTION OF THE DRAWING

The accompanying photograph illustrates the distinguishing traits of *Griselinia* 'Green Hedgemaster'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Griselinia* cultivar named 'Green Hedgemaster'. Data was collected in Auckland, New Zealand from 2 year old field grown plants. The time of year was Winter in the Southern Hemisphere and the average temperature range was 12 to 18 degrees Centigrade during the day and 4 to 11 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Green Hedgemaster' has not been tested under all possible conditions and phenotypic differences may be observed with variations in environmental, climatic, and cultural conditions, however, without any variance in genotype.

Botanical classification: *Griselinia littoralis* 'Green Hedgemaster'.
Use: Ornamental perennial shrub.
Parentage: 'Green Hedgemaster' is a naturally occurring branch mutation of *Griselinia* 'Variegata'.
Vigor: Vigourous.
Growth rate: 1.0 meter per year.
Growth habit: Semi upright.
Plant shape: Oval.
Suitable container size: 2.0 liter container.
Height: Average 8.0 m in height.
Width: Average 4.0 m in width.
Hardiness: Tolerant to −7 degrees Centigrade.
Propagation: Tip cuttings.
Time to initiate roots: Approximately 50 days in the Summer and 60 days in the Winter.
Time to produce a rooted cutting: Approximately 84 days in the Summer and 95 days in the Winter.
Root system: Fine and fibrous.
Lateral Branches:
*Quantity.*—Approximately 60.
*Length.*—Average 0.25 m.
*Diameter.*—Average 5 mm.
*Internode length.*—35 mm.
*Shape.*—Rounded.
*Color.*—46A when young turning to 152D when mature.
*Strength.*—Strong.
*Pubescence.*—Absent.
*Pinching.*—Yes.
Foliage:
*Texture.*—Leathery.
*Leaf arrangement.*—Alternate.
*Compound or single.*—Single.
*Quantity of leaves per lateral branch.*—Varies between 2 and 9.
*Leaf shape.*—Orbicular.
*Leaf shape.*—Rounded.
*Leaf base.*—Obtuse.
*Leaf lengthy.*—Average 70 mm in length.
*Leaf width.*—Average 55 mm in width.
*Pubescence.*—Absent.
*Leaf margin.*—Entire.
*Young leaf color* (*upper surface*).—144A.
*Young leaf color* (*lower surface*).—144B.
*Mature leaf color* (*upper surface*).—144A.
*Mature leaf color* (*lower surface*).—144B.
*Vein color* (*both surfaces*).—N144A.
*Petiole length.*—11 mm.
*Petiole diameter.*—3 mm.
*Petiole color.*—N144A.
*Petiole texture.*—Leathery.
*Durability of foliage to stress.*—Moderate to high.
*Flowers.*—No flowers have been observed to date.
*Disease and Insect Resistance.*—Plants of the new *Griselinia* have not been observed for disease or insect resistance.

What is claimed is:

1. A new and distinct variety of *Griselinia* plant named 'Green Hedgemaster' as described and illustrated.

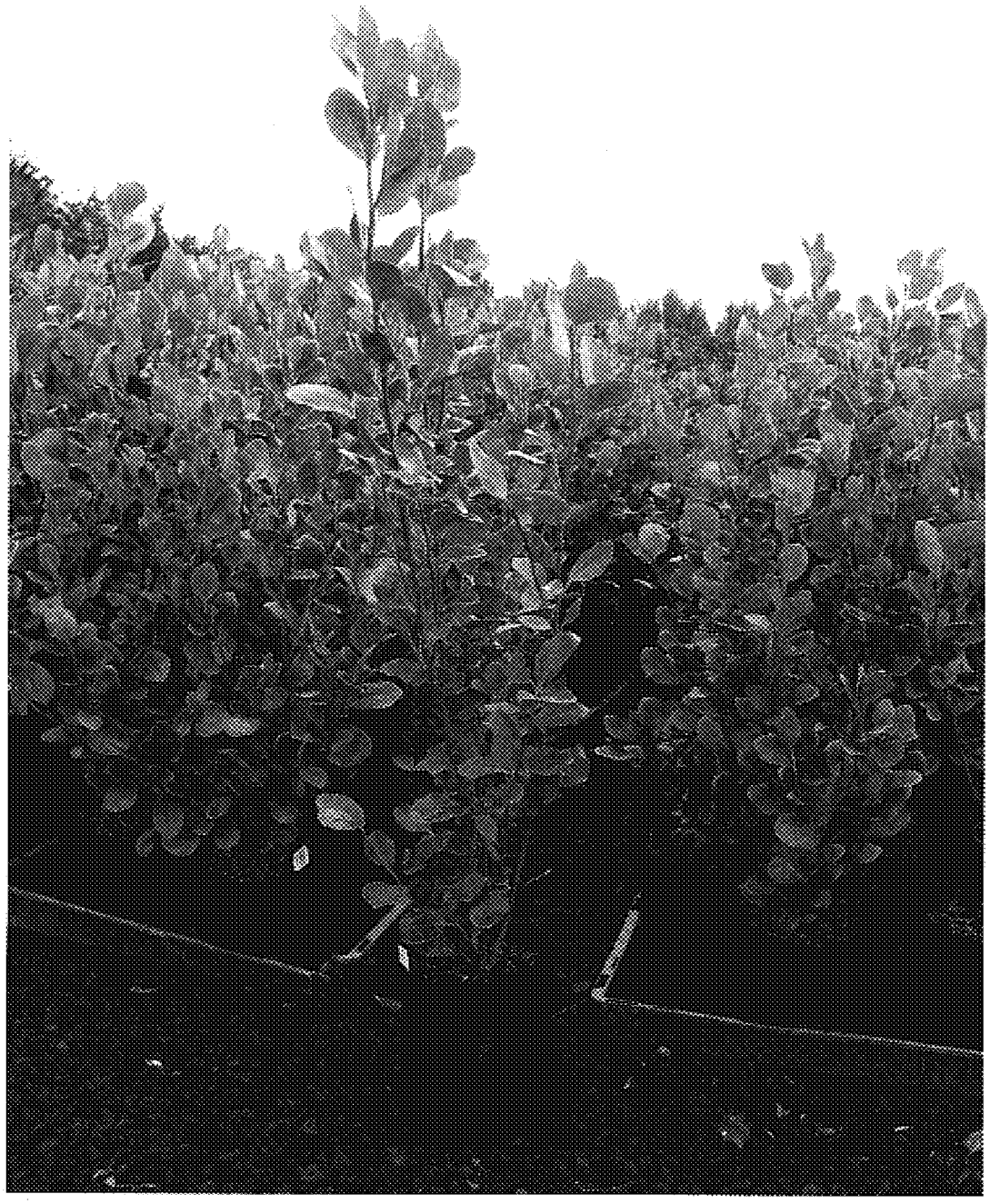

* * * * *